United States Patent
Page et al.

(10) Patent No.: US 7,621,606 B2
(45) Date of Patent: Nov. 24, 2009

(54) TRANS-DIFFERENTIATION AND RE-DIFFERENTIATION OF SOMATIC CELLS AND PRODUCTION OF CELLS FOR CELL THERAPIES

(75) Inventors: Raymond Page, Southbridge, MA (US); Tanja Dominko, Southbridge, MA (US); Christopher Malcuit, Hudson, MA (US)

(73) Assignee: Advanced Cell Technology, Inc., Worcester, MA (US)

( * ) Notice: Subject to any disclaimer, the term of this patent is extended or adjusted under 35 U.S.C. 154(b) by 0 days.

(21) Appl. No.: 10/228,296

(22) Filed: Aug. 27, 2002

(65) Prior Publication Data
US 2003/0059939 A1 Mar. 27, 2003

Related U.S. Application Data

(60) Provisional application No. 60/314,654, filed on Aug. 27, 2001.

(51) Int. Cl.
C12N 5/00 (2006.01)
C12N 5/02 (2006.01)
C12N 5/08 (2006.01)
C12N 5/16 (2006.01)

(52) U.S. Cl. .................... 425/377; 435/325; 435/368; 435/384

(58) Field of Classification Search .............. 435/377, 435/371, 372, 368, 366, 384, 325
See application file for complete search history.

(56) References Cited

U.S. PATENT DOCUMENTS

| | | | |
|---|---|---|---|
| 5,166,317 A | 11/1992 | Wallace et al. | |
| 5,480,772 A | 1/1996 | Wangh | |
| 5,651,992 A | 7/1997 | Wangh | |
| 5,830,651 A | 11/1998 | Cauley et al. | |
| 6,011,197 A | 1/2000 | Strelchenko et al. | |
| 6,197,743 B1 * | 3/2001 | Faller | 514/2 |
| 2001/0012513 A1 | 8/2001 | Robl et al. | |
| 2002/0142397 A1 | 10/2002 | Collas et al. | |

(Continued)

FOREIGN PATENT DOCUMENTS

JP 63044526 2/1988

(Continued)

OTHER PUBLICATIONS

Zinzar et al, Azacytidine plus verapamil induces the differentiation of a newly characterized biphenotypic human myeloid-B lymphoid leukemic cell line BW-90, Leukemia Research, 1998, vol. 22, pp. 677-685.*

(Continued)

*Primary Examiner*—Maria Marvich
(74) *Attorney, Agent, or Firm*—Hunton & Williams (57) ABSTRACT

The invention provides a method for effecting the trans-differentiation of a somatic cell, i.e., the conversion of a somatic cell of one cell type into a somatic cell of a different cell type. The method is practiced by culturing a somatic cell in the presence of at least one agent selected from the group consisting of (a) cytoskeletal inhibitors and (b) inhibitors of acetylation, and (c) inhibitors of methylation, and also culturing the cell in the presence of agents or conditions that induce differentiation to a different cell type. The method is useful for producing histocompatible cells for cell therapy.

15 Claims, 6 Drawing Sheets

U.S. PATENT DOCUMENTS

| | | | |
|---|---|---|---|
| 2003/0044976 A1 | 3/2003 | Dominko et al. | |
| 2003/0046722 A1 | 3/2003 | Collas et al. | |
| 2003/0199535 A1* | 10/2003 | Cavazza et al. | 514/283 |
| 2004/0087652 A1* | 5/2004 | Gottlicher et al. | 514/558 |
| 2005/0014258 A1* | 1/2005 | Collas et al. | 435/455 |

FOREIGN PATENT DOCUMENTS

| | | |
|---|---|---|
| WO | WO97/35967 | 10/1997 |
| WO | WO99/05266 | 2/1999 |
| WO | WO00/65137 | 11/2000 |
| WO | WO01/46401 | 6/2001 |

OTHER PUBLICATIONS

Unemori and Werb, Reorganization of Polymerized Actin: A Possible Trigger for Induction of Procollagenase in Fibroblasts Cultured in and on Collagen Gels, Journal of Cell Biology, 1986, vol. 102, pp. 1021-1031.*

Thiebot et al, Drug-induced alterations in rat peritubular cell cytoskeleton result in proteoglycan synthesis modifications. Comparison with some intracellular signaling pathways, Biology of the Cell 91 (1999) 117-129.*

Haynes and Weller, The Effects of Cytochalasin B and Colchicine on Cell Motility and Ultrastructure in Primary Cultures of Malignant Gliomas, Acta Neuropathol. (Berl.) 44, 21-30 (1978).*

Sauman and Berry, Cytochalasin-D treatment triggers premature apoptosis of insect ovarian follicle and nurse cells, Int. J. Dev. Biol. 37: 441-450 (1993).*

Bodnar et al., "Extension of life-span by introduction of telomerase into normal human cells", Science 279:349-352 (1998).

Wilmut et al., "Viable offspring derived from fetal and adult mammalian cells", Nature 385:810-813 (1997).

Smith et al., "Cytoplasmic transfer of the mitogenic response to platelet-derived growth factor", Proc. Nat'l Acad. Sci. USA 78:4363-4367 (1981).

Ziegler, "Phenotypic expression of malignancy in hybrid and cybrid mouse cells", Somatic Cells Genetics 4:477-489 (1978).

Lanzendorf et al., "Pregnancy following transfer of ooplasm from cryopreserved-thawed donor oocytes into recipient oocytes", Fertility and Sterility 71:575-577 (1999).

Willadsen, "Nuclear transplantation in sheep embryos", Nature 320:63-65 (1986).

Thomson et al., "Embryonic stem cell lines derived from human blastocysts", Science 282:1145-1147 (1998).

Dominko et al., "Bovine oocyte cytoplasm supports development of embryos produced by nuclear transfer of somatic cell nuclei from various mammalian species", Biol. Reprod. 60:1496-1502 (1999).

Collas, "Cytoplasmic control of nuclear assembly", Reprod. Fertil. Dev. 10:581-592 (1998).

Katagiri et al., "Remodeling of sperm chromatin induced in egg extracts of amphibians", Int. J. Dev. Biol. 38:209-216 (1994).

Dimitrov et al., "Remodeling somatic nuclei in Xenopus laevis egg extracts: molecular mechanisms for the selective release of histones H1 and H1(0) from chromatin and the acquisition of transcriptional competence". EMBO J. 15:5897-5906 (1996).

Maxson et al., "Differential stimulation of sea urchin early and late H2B histone gene expression by a gastrula nuclear extract after injection into Xenopus laevis oocytes", Mol. Cell. Biol. 8:1236-1246 (1988).

Wangh et al., "Efficient reactivation of Xenopus erythrocyte nuclei in Xenopus egg extracts", J. Cell Sci. 108:2187-2196 (1995).

Hansis et al., "Nuclear reprogramming of human somatic cells by xenopus egg extract requires BRG1", Curr. Biol. 14:1475-1480 (2004).

Bain et al., "Embryonic stem cells express neuronal properties in vitro", Dev. Biol. 168:342-357 (1995).

Fricker et al., "Site-specific migration and neuronal differentiation of human neural progenitor cells after transplantation in the adult rat brain", J. Neurosci. 19:5990-6005 (1999).

Prather et al., "Nuclear Transplantation in Early Pig Embryos", Biol. Reprod. 41:414-418. (1989).

Hornsby et al., "Redifferentiation, cellular elongation and the cell surface during lens regeneration", J. Embryol. Exp. Morph. 39(1):23-43 (1977).

Thesingh et al., "Transdifferentiation of hypertrophic chondrocytes into osteoblasts in murine fetal metatarsal bones, induced by co-cultured cerebrum", Bone and Mineral 12(1):25-40 (1991).

Hakelien et al., "Novel approaches to transdifferentiation", Cloning and Stem Cells 4(4):379-387 (2002).

Tung et al, "Characterization of Rat Testicular Peritubular Myoid Cells in Culture: α-Smooth Muscle Isoactin Is a Specific Differentiation Marker", Biol. of Reprod. 42:351-365 (1990).

* cited by examiner

TRANS-DIFFERENTIATION AND RE-DIFFERENTIATION OF SOMATIC CELLS AND PRODUCTION OF CELLS FOR CELL THERAPIES

RELATED APPLICATIONS

This application claims benefit of priority to U.S. Ser. No. 60/314,654 filed on Aug. 27, 2001 which is incorporated by reference in its entirety herein.

FIELD OF THE INVENTION

This application relates to methods for effecting trans-differentiation of somatic cells. Trans-differentiation is the conversion of a cell from one differentiated cell type to another differentiated cell type.

BACKGROUND OF THE INVENTION

Stem cells obtained from adults (mesenchymal, hematopoietic, neuronal) are receiving increasing interest as a source of material for cell and tissue transplantation to treat human disease. To a large degree, this interest has been stimulated by findings that report the presence of certain types of stem cells in unexpected tissue compartments in vivo (e.g. neuronal stem cells in bone marrow). In addition, some types of stem cells are displaying an unanticipated plasticity in their ability to trans-differentiate into other types of cells when transplanted from their niche into heterologous tissue compartments. Despite these developments, problems of stem cell accessibility and quantity persist.

The transdifferentiation potential of adult cells has also been receiving increasing attention during the past few years (Eguchi and Kodama, 1993). Trans-differentiation is a physiological process that occurs during development but has also been described in a number of adult organs including liver, thyroid, mammary gland (Hay and Zuk, 1999), and kidney (Strutz et al., 1995). It has been shown that alteration of cell morphology and function can be induced artificially in vitro by treatment of cell cultures with cytoskeletal disruptors, hormones, and Calcium-ionophores. Trans-differentiation is a physiological process that occurs during development, and has also been described in a number of adult organs including liver, thyroid, mammary gland (Hay and Zuk, 1999), and kidney (Ng et al., 1999). Alteration of cell fate can be induced artificially in vitro and there is a vast amount of published data describing trans-differentiation. For example, embryonic blastomeres can be induced to differentiate in the presence of microfilament inhibitors (Okado and Takahashi, 1988, 1990; Wu et al., 1990; Pratt et al., 1981). Supplementing growth media for somatic cells with cytoskeletal inhibitors (Brown and Benya, 1988; Takigawa et al., 1984; Shea, 1990; Tamai et al., 1999; Cohen et al., 1999; Fernandez-Valle et al., 1997; Yujiri et al., 1999; Ulloa and Avila, 1996; Ferreira et al., 1993; Sato et al., 1991; Zanetti and Solursh, 1984; Kishkina et al., 1983; Hamano and Asofsky, 1984; Holtzer et al., 1975; Cohen et al., 1999), Ca-ionophores (Shea, 1990; Sato et al., 1991), corticosteroids (Yeomans et al., 1976), and DMSO (Hallows and Frank, 1992), causes changes in cell shape and function. Mammary epithelial cells can be induced to acquire muscle-like shape and function (Paterson and Rudland, 1985), spleen cells can be induced to produce both IgM and IgG immunoglobulins (van der Loo et al., 1979), pancreatic exocrine duct cells can acquire insulin-secreting, endocrine, phenotype (Bouwens, 1998a,b), 3T3 cells into adipose cells (Pairault and Lasnier, 1987), mesenchymal cells into chondroblasts (Rosen et al., 1986), bone marrow cells into liver cells (Theise et al., 2000), islets into ductal cells (Yuan et al., 1996), muscle into 7 non-muscle cell types, including digestive, secretory, gland, nerve cells (Schmid and Alder, 1984), muscle into cartilage (Nathanson, 1986), neural cells into muscle (Wright, 1984), bone marrow into neuronal cells (Black, 2000). However, complete conversion to a fully functional and stable different type of cell has never been demonstrated.

DESCRIPTION OF THE DRAWINGS

FIG. 1: (A) Control, (B) 2.5 µg/ml, (C) 5.0µg/ml, (D) 7.5 µg/ml FIGS. 3A and B and FIGS. 4A, B, C, and D: Cells with neuronal morphology produced by treating bovine adult fibroblasts CB at 10.0 µg/m and culturing them under conditions that induce neural differentiation.

(A) Control, (B) 2.5 µg/ml, (C) 5.0 µg/ml, (D) 7.5 µg/ml

DESCRIPTION OF THE INVENTION

The objective of this invention is to develop technology for trans-differentiation of cells in vitro that does not utilize early preimplantation embryos, fetal tissues, or adult stem cells and can be customized for individual patients using their own cells as donors.

The present invention utilizes a cell's ability to respond to environmental factors after they have been "primed" to do so in vitro. Priming is achieved by destabilizing cell's cytoskeletal structure, consequently removing the feedback mechanisms between cell's shape and nuclear function. Both, shape and function define the specificity of any cell type. The human cell types used as a source are differentiated somatic cells, such as fibroblasts and keratinocytes from skin biopsies, and leukocytes from blood samples. Cell structure is first destabilized with cytoskeletal inhibitors, consequently their nuclear structure becomes permissive to alteration and upon exposure to conditions that promote or support a desired cell type such that the primed cells acquire this new morphology and function. Primed cells are multipotent and, upon application of factors that induce formation of the central nervous system are capable of differentiating into different neurons, astrocytes, or oligodendrocytes. The result is populations of newly differentiated neuronal cell types genetically identical to the fibroblasts sampled from the donor. The present invention overcomes barriers and limitations to the derivation of patient-specific cells, which are: the need for embryos as a source of embryonic stem cells, histo-incompatibility between the donor and the recipient, the risk of transmitting animal viruses via xenotransplantation, insufficient quantities of cells/tissues for transplantation, and high cost associated with generation of embryos and embryonic stem cells, life-long immunosuppression, and the requirement for repeated treatments.

The methods of the present invention can be used to effect trans-differentiation of any type of somatic cell into any other type of somatic cell. Examples of such cells that may be used or produced include fibroblasts, B cells, T cells, dendritic cells, keratinocytes, adipose cells, epithelial cells, epidermal cells, chondrocytes, cumulus cells, neural cells, glial cells, astrocytes, cardiac cells, esophageal cells, muscle cells, melanocytes, hematopoietic cells, macrophages, monocytes, and mononuclear cells.

The cells used with the methods of the invention may be of any animal species; e.g., mammals, avians, reptiles, fish, and amphibians. Examples of mammalian cells that can be trans-differentiated by the present invention include but are not limited to human and non-human primate cells, ungulate cells, rodent cells, and lagomorph cells. Primate cells with which the invention may be performed include but are not limited to cells of humans, chimpanzees, baboons, cynomolgus monkeys, and any other New or Old World monkeys. Ungulate cells with which the invention may be performed include but are not limited to cells of bovines, porcines, ovines, caprines, equines, buffalo and bison. Rodent cells with which the invention may be performed include but are not limited to mouse, rat, guinea pig, hamster and gerbil cells. Rabbit cells are an example of cells of a lagomorph species with which the invention may be performed.

The present invention is a method by which cells of one differentiated cell type can be converted to a different differentiated cell type without necessarily reverting to a stem-like cell intermediate. This may be done without losing cell viability, and while and allows the converted cells to retain their overall biochemical activity and chromatin stability.

The invention comprises sequentially evaluating each of the steps required for trans-differentiation. The steps include: 1. growth of primary cell cultures, effectiveness and reliability of "priming" agents, assessment of the primed state in vitro, 2. the ability of primed cells to trans-differentiate upon induction, 3. design reproducible and reliable induction protocols, 4. ability to maintain stable cell function, and 5. the ability of newly trans-differentiated cell types to interact with patient's cells upon cell transplantation. Primed and newly induced cell types can be characterized for their gene expression, cell surface antigens, morphology, excitability, secretory function, synapse formation, and stable functional grafting in the rat model for Parkinson's disease.

Abbreviations

3-D-three dimensional
BFFs-bovine fibroblasts
bFGF-basal fibroblast growth factor
BMP-2-bone morphogenic protein-2
CalR1-glial marker
CB-cytochalasin B
CD14-lipopolysacharide receptor
CD34-leukocyte common antigen
CD45-blood cell marker
CNF-necrosis factor
CNS-central nervous system
CNTF-cilia neurotropic factor
BSA-bovine serum albumin
ECM-extracellular matrix
ESC-embryonic stem cells
FCS-fetal calf serum
GFs-growth factors
DMEM-Dulbecco's modified minimum essential medium
DMSO-dimethylsulfoxide
EGF-epidermal growth factor
En-1-enolase
FGFR3-fibroblast growth factor receptor 3
G1/G0-gap phases of the cell cycle
GABA-gamma-amino butyric acid
GFAP-glial fibrilarin associated protein
HPLC-high pressure liquid chromatography
ICC-immunocytochemistry
ICM-inner cell mass
IgG-immunoglobulin G
Nurr-1-nuclear receptor
Pax8-neuronal inducer
PDGF-platelet derived growth factor
PERVS-porcine endogenous retroviruses
RT-PCR-reverse transcription-polymerase chain reaction
SCID-severe combined immunodeficiency
SHH-sonic hedgehog
T3-tyroxin
TH-tyrosine hydroxylase
TUJ1-glial marker Pharmaceutical strategies for treating a variety of neuronal disorders are currently available, but all of these organic chemicals have limitations in their clinical efficacy. For example, the most widely used drug for treatment of Parkinson's disease, Levodopa□ is a dopamine precursor and results in increased dopamine production from dopaminergic neurons. However, side effects of Levodopa□ are debilitating and include hallucination, severe nausea, and vomiting. Long-term use results in induction of tolerance, which in turn translates to increasing doses over time, ultimately leading to a lower clinical benefit to risk ratio. Treatment of brain disorders using biologics is not practical since the therapeutic agent must cross the blood-brain barrier, which does not happen for most proteins and peptides present in the bloodstream. Due to the limitations of traditional pharmaceutical and biologic intervention, alternative approaches are being pursued aggressively. Recent advances in in vitro cell culture and manipulation technology have led to the prospect of using cell transplantation as a means for restoring cells or tissues that have been damaged due to progression of disease. This approach not only offers the prospect of treating the disease, but also may ultimately provide a cure, if the grafted cells become fully integrated and functional upon transplantation into the host tissue. Currently, there are three major target areas for obtaining material for cell transplantation therapy for treatment of candidate diseases such as Parkinson's disease and other neurological disorders. Each of these approaches is discussed in turn.

First, recent derivation of both monkey and human embryonic stem-like cells from blastocyst inner cell masses has enabled investigation of differentiation events that has not been possible in primates before. Embryonic stem-like cells have been shown to develop into lineages of all three germ layers in vitro. Consequently, many research groups are focusing their resources on the use of therapeutic cloning approaches, which uses mammalian oocytes as a vehicle to exploit factors important for genomic reprogramming. However, the potential use of specialized cells derived from ES-like cells for allo-transplantation in humans has yet to be evaluated (Bain et al., 1995; Brustle et al., 1999; Fairchild et al., 1995; Keller, 1995).

Second, an alternative approach to provide patients with highly specialized cell types relies on a non-embryonic stem cell as an intermediate. Populations of tissue-specific progenitor cells, such as mesenchymal, hematopoietic, and neuronal stem cells are obtained from specific locations within an adult human patient. These adult tissue-specific stem cells have been isolated, propagated in vitro, and astonishing progress has been achieved in differentiation of mesenchymal and neuronal precursors into adipocytic, chondrocytic, osteocytic cells, blood cells, and neurons, respectively (Pittenger et al., 1999; Black et al., 2000). Using this approach, histo-incompatibility between donor cells and recipient is alleviated. A major disadvantage is that the process requires cumbersome clinical and laboratory procedures that are not fully established to obtain sufficient quantities of progenitor stem cells from adults.

Finally, a third strategy involves xeno-transplantation using pig cells as donors. The most advanced program involves obtaining neurons from pig fetuses and transplanting them into human patients with minimal in vitro manipulation. On average, 8 fetuses are required for treatment of a single patient, which limits usefulness of this approach (Studer, personal communication). In addition, recent concern over transmission of porcine viruses to humans has slowed otherwise effective and promising research in this area (Imaizium et al., 2000).

Despite these discoveries, the path to development of various tissue specific cell types without embryonic or other stem cells as an intermediate requirement has not been described. Consequently, there are strong justifications across the entire spectrum of biomedical research for developing alternative methods for production of patient-compatible or autologous specific cell types. A reliable source of cells would be needed to treat millions of patients affected with Parkinson's disease, Huntington's disease, Alzheimer's disease, Multiple Sclerosis, spinal cord injuries, stroke, burns, heart disease, diabetes, arthritis, and many genetic and other disorders that could benefit from cell/tissue therapy. The ability to use embryonic and/or adult stem cells in reliable and efficient strategies for the production of specialized cell types and tissues for human cell/tissue therapy remains to be shown. Notwithstanding these successes and exciting prospects, the problem of histo-incompatibility between the donor and the recipient of stem cells remains unsolved, as does the availability of preimplantation embryos for the derivation of embryonic stem cells.

Various types of differentiated neuronal cells can be generated from a single type of somatic cell taken from an individual donor (primary cell cultures) and the resulting cells transplanted into the same individual. The present invention provides methods for effecting trans-differentiation of highly specialized somatic cells (e.g. skin fibroblasts) into different, fully functional specialized cells (dopaminergic neurons, astrocytes, oligodendrocytes, GABA neurons, serotonin neurons, acetylcholin transferase neurons, etc.) in vitro. The present invention does not utilize any part of an oocyte, an early preimplantation embryo or fetal tissue as a vehicle for de-differentiation and reprogramming. It can be customized for individual patients.

The present invention exploits the fact that all the cells of an individual contain all the genetic information required for development. Expression of specific genes that define a cell's morphology and function is determined largely by genetic programming and environmental signals, but can be altered upon environmental insults (as in wound healing, bone regeneration, and cancer). In order to change the function of the cell, the present invention uses cytoskeletal disruptors for "priming" of differentiated cells. Our hypothesis is that priming alters the cytoskeleton, which disrupts the cell's transport machinery, and ultimately interferes with the cell type-specific feedback mechanisms the nucleus receives from the cell's periphery. This disruption allows the nucleus to become responsive to different or alternative clues from its environment. After priming, cells are exposed to an environment that induces and supports differentiation into the desired cell type (i.e. neurobasal medium for neurons).

The benefits of the present invention are significant and include:
(i) No need for embryos or fetal tissue. With the present invention, human embryos do not have to be created, destroyed, or used to generate trans-differentiated cells, thus eliminating the cost of production, time constraints, and the concern over ethical issues.
(ii) No need for patient immuno-suppression. Efficacious allo- and xeno-cell therapy protocols have been demonstrated in many pre-clinical animal models and in some clinical human subjects. However, in most cases, extended graft survival (beyond a few days) has only occurred when combined with pharmaceutical immuno-suppression. This includes cases where the cells are encapsulated with artificial matrix materials, such as alginate, which is designed to exclude histocompatibility molecules. While the matrix encapsulation approach may reduce short-term graft rejection, eventually the transplanted cells are destroyed due to nutrient and oxygen deprivation, which results from pericapsular fibrosis. This results in the need for repeated treatment. Therefore, a preferred method of long term and lasting treatment using cell-based therapy would involve cells originally derived from the patient.
(iii) No health risks due to possible transmission of animal viruses. The present invention avoids the concerns in xenotransplantation regarding porcine endogenous retroviruses (PERVS). PERVS are ancestral genes located in the porcine genome that resulted from retroviral DNA integration. There is a possibility of that the presence of porcine cells in the human body could induce PERV expression in an immuno-suppressed patient that might lead to recombination, thus, producing new pathogens. This would pose a new health threat not only to the patient, but also to the surrounding population if the new virus were to be communicable. Since no component of an animal cell is ever used in the invention, threats due to animal genomic DNA sequences such as PERVS are not a concern.
(iv) Availability of large numbers of specialized cells in a relatively short time. The present invention contrasts with embryonic methods, which have yielded only small numbers of starting stem cells (between 10-15 cells from a blastocyst). The current strategies being developed by our competitors (Geron, Menlo Park, Calif.) utilize established human embryonic stem cell lines as the basis for their product. Since the number of cells used to derive the initial cell line is so low, a vast amount of in vitro proliferation will have to take place to satisfy the needs of the millions of patients to be treated with cell therapy. It is known that extensive proliferation in vitro results in acquired genetic mutations and even spontaneous imortalization. Since in the present invention large numbers of cells are be harvested from individual patients (a single, common source of stem cells is not required any longer) as starting material, the degree of in vitro proliferation is only what is needed to prime the cells, trans-differentiate them and generate enough cells for a needed clinical application.
(v) Lower cost. The present invention will significantly reduce the cost of cell therapy by eliminating the need for immuno-suppression of the patient to reduce hyper-acute (in xeno-transplantation) and delayed rejection (in allo- and xeno-transplantation). Using current transplantation regimes, patients depend on lifetime immuno-suppressive therapy, which is not only costly, but results in increased risk of infections, and lower quality of life. The need for repeated transplantation procedures would likely also be alleviated.

Efficacy of the Invention

Donor cells are treated by the invention in a way that "primes" them for trans-differentiation without reverting them necessarily to stem-like cells. This is done without losing cell viability and allowing them to retain their overall biochemical activity and chromatin stability; in short, to ensure the cells can retain their overall functionality.

In vivo, differentiated cell types vary in their ability to undergo proliferation and continue cycling upon physiological demand. Several cell types are known to be terminally arrested in the G0 phase of the cell cycle and do not proliferate after birth. Examples are heart smooth muscle cells, neurons, Sertoli cells in male testes, and oocytes in female ovaries. Other cell types, however, have been known to have high regeneration ability that is retained during the post-natal period. They include liver cells, several connective tissue cell types (cartilage, bone, and fibroblasts), epithelia (skin and gut); hematopoietic cells (bone marrow and spleen) and this regeneration response can generally be induced by trauma. Not only can these cells regenerate themselves but can also generate cells of distinctly different phenotypes. Transdifferentiation potential of adult cells has been receiving increasing attention during the past few years (Eguchi and Kodama, 1993; Strutz and Muller, 2000).

This invention describes technology for trans-differentiation of one type of somatic cell into another using in vitro culture with cytoskeletal inhibitors (cytochalasins A, B, D and E, latrunculin, jasplakinolide, etc). It further describes technology for maintenance of the newly trans-differentiated cell types, stable cell morphology and cell-specific gene and protein expression. The utility of the present invention is in developing specific growth factor, matrix and cytokine combinations that reliably direct differentiation into a desired cell type. This provides autologous (isogeneic) cell types for cell transplantation in the same individual that donated the initial somatic cell sample. The present invention overcomes immune rejection by the cell transplantation recipient, significantly shortens the time required for the "new" cells to be available for therapy, does not use embryo or fetus intermediaries as vehicles for reprogramming, and does not require generation of embryonic or any other stem cell precursors. The present invention produces cells that are primed to develop into neuronal cell lineages. During the period of time when the cells are being "primed" they may be used as partially de-differentiated cells for derivation of other, non-neuronal cell types.

Description of Inventive Methodology

1. Develop an Interaction Matrix between Donor Cell Type, Optimal Cell Cycle Stage and the Priming Agent.

Rationale: Terminally differentiated somatic cells of the vast majority of mammalian tissues lose their genomic plasticity during development. Cells are characterized to belong to a specific tissue based on their location in vivo, their morphological appearance (shape and size), expression of specific proteins, and specialized function. Some of these characteristics are retained when cells are isolated from an individual and propagated in culture. Conditions that support extensive expansion of various cell types in culture are well established, as are requirements for maintenance of their morphology and function largely due to the fact that maintenance of the desired cell type was the experimental goal (Basic Cell Culture Protocols, 1997). It has also been recognized that among factors that determine a cell's fate during development and differentiation, the environment and clues received from neighboring cells and extra-cellular matrix (Hohn and Denker, 1994) not only promote proliferation of certain cell types but also determine their terminally differentiated phenotype (Fuchs et al., 2000). Several cell types can be induced to trans-differentiate in culture, such as bone marrow into brain cells (Black et al., 2000) and liver (Theise et al., 2000), muscle into chondrocytes (Nathanson, 1986), thyroid cells into neurons (Clark et al., 1995), and mammary epithelium into muscle (Paterson and Rudland, 1985). Though possible, trans-differentiation of fibroblasts has not been examined, and a "primed" state that allows trans-differentiation to occur has not been described for any cell type.

Experimental: Factorial experiments can be designed to investigate the interactions between donor cell type, primer, the concentration of the primer, duration of priming and the cell cycle stage of the donor cell. Human primary keratinocytes, fibroblasts, leukocytes, and liver cells obtained from commercially available sources (Clonetics, Calif. and ATCC, Rockville, Md.), will be grown in vitro and expanded to $1 \times 10^7$ using standard cell culture conditions (DMEM, supplemented with amino acids, L-glutamine, β-mercaptoethanol, 10% fetal calf serum; Gibco, Gaitherburg, Md.). Cultures will be supplemented with and increasing dose of cytochalasin B (CB, 0.1-10 µg/ml; Sigma Chemical Co, St. Louis, Mo.) and cells' morphology recorded at 12-hour intervals over a period of 72 hours. Control cells can be grown in vitro in the absence of the inhibitor or in the presence of DMSO (Sigma) alone, which is used to solubilize CB. At the same experimental time points, cells will be examined for down-regulation/loss of their specific gene/protein expression by RT-PCR and immuno-cytochemistry (ICC) according to published protocols. The majority of the oligonucleotide primers and antibodies for these studies are commercially available. Some of the markers are summarized in Table 1. In parallel, the effect of other microfilament inhibitors (cytochalasin A, D and E) will be examined at concentrations and times described above.

Cells are synchronized in G1, S, G2, and M-phase of the cell cycle using published protocols (Leno et al., 1992). Briefly, growing primary cultures are synchronized by an initial S phase block for 20 hours with 2.5 mM thymidine, followed after a 5 hour interval by a 9 hour mitotic block by demecolcine. Mitotic cells are shaken off and mitotic index checked on cytospin prepared slides. Double thymidine block (thymidine for 17 hours, release for 9 hours, thymidine for 15 hours) are used for synchronization of cells at the beginning of S phase. Seven hours after release of the second thymidine block, cells are expected to accumulate in G2. Synchronized cell populations are then exposed to CB as described for non-synchronized, randomly cycling cell populations.

TABLE 1

Donor cell types and associated endogenous, phenotype-specific markers.

| Donor cell type | Endogenous markers |
| --- | --- |
| Skin fibroblasts (mesoderm) | FSP-1, vimentin, fibronectin |
| Keratinocytes (ectoderm) | keratin, melanin |
| Hepatocytes (endoderm) | fibrinogen, albumin, cytokeratins 8, 18, 19 |
| Blood cells (mesoderm) | immunoglobulins, CD antigens |

Data Collection and Analysis: Changes in cell shape and general morphology are used as the first indicator of "priming" and images sequentially recorded by time lapse video imaging (cooled CCD camera, 40× magnification, DIC optics on an upright Olympus, Metamorph imaging software). Patterns of the down-regulation/loss of primary cell-specific gene expression and consequently protein synthesis are evaluated by RT-PCR and ICC and compared to control primary cells that were grown in culture for the same period of time, but were not exposed to the inhibitor, or were exposed to the same concentration of DMSO, which is used as a solvent for cytochalasin B.

Adherent cells, such as fibroblasts will change morphology due to cytoskeletal inhibition. Cells grown in suspension (blood cells) may display less or no morphological alteration. It is likely that cells will continue with nuclear progression through the cell cycle and karyokinesis, while cytokinesis will be inhibited. Depending on the dose of CB, cells may complete one or more rounds of DNA replication and karyokinesis in the absence of cell division. Cells "primed" with cytochalasin B lose their cell-specific gene expression, and this down-regulation is expected to correlate with the concentration of the priming agent and the duration of exposure. There are advantages and disadvantages of both low and high CB concentration priming protocols. Lower concentrations of CB may induce slow, step-by-step disruption of cellular architecture. This would in turn allow cells to gradually decrease cellular transport of tissue-specific factors to their cytoplasmic or plasma membrane targets. If inhibition is then maintained over an extended period of time, function of the cell's nucleus will gradually become deprived of feedback signals originating from target sites.

Without this feedback regulation, the nucleus would adopt a different gene expression profile which becomes less dependent on clues received from the immediate environment. A potential disadvantage of the low dose protocol is that viability of cells may decline, as the incubation time has to be lengthened. The environment can be manipulated in such a way that factors which are beneficial for neuronal development (ascorbic acid, all-trans retinoic acid, neuro-basal growth medium, bFGF and fibronectin) will allow for gradual, instead of abrupt, imposition of the cell to change. On the other hand, high concentration of CB for shorter period of time may be advantageous when high amounts of specific protein are required for a short period of time to maintain cell function (such as hormone secreting, endocrine cells). During exposure to high concentrations of CB, cells continue to replicate their DNA and progress through mitosis (karyokinesis) in the absence of cytokinesis only once. Multiple nuclei within primed cells are expected after low dose protocol and effect of multiple nuclei on cell function will have to be evaluated. Under high concentrations of CB binucleated cells are expected to be the predominant outcome. In addition to cell type, the stage of the cell cycle during which a particular cell type is exposed to "primers" will result in different outcomes after priming. Our preliminary results show that cells can be kept viable for at least 72 hours in the presence of CB without detrimental effects on their survival.

Experiments can be performed using the methodology disclosed herein to test various values of parameters influencing the trans-differentiation process to develop a database of interactions. Such a database will permit one to predict the results of using a specific cell type, a specific primer, specific concentration and time of exposure, in terms of obtaining a cell of a desired morphology and gene down-regulation pattern.

It has been shown that DMSO can induce change of function on its own (Hallows and Frank, 1992). If control experiments indicate that this is indeed a possibility, we will examine effect of DMSO alone in more detail and design experiments accordingly. Using the disclosed methods, we have found that fibroblasts respond to CB treatment with a high degree of repeatability and that virtually all the cells display a change in phenotype, making them a cell type of choice for trans-differentiation. However, alternative cell types such as keratinocytes or white blood cells can also be used. Source cells selected for use should be easy to obtain, with minimal invasion and discomfort for the patient. If no distinct differences can be found between different donor cell types, fibroblasts can be used.

Different cytoskeletal inhibitors will induce distinctly different alteration in cells during priming. Cytoskeletal inhibitors that are suitable for use in the present invention include microfilament disruptors (e.g., cytochalasin B, D, A, E; vimentin, latrunculin, jasplakinolide). These inhibitors act through different cellular targets in order to depolymerize microfilament network and a specific mode of action may be advantageous/disadvantageous for "priming" purposes. Different priming agents are expected to induce different "primed" state: for example, CB may be "priming" cell for neuronal development while cytochalasin D may be "priming" the same cells to undergo hematopoietic development (confidential preliminary data, not disclosed).

Microtubule inhibitors, such as colchicine, colcemid, nocodazole, and taxol, can also be used as primers in the present invention. They can be used at concentrations that have been shown to induce a change of cell function (Cohen et al., 1999). Priming agents can be used alone or in combination. For example, one or more microtubule inhibitors may be used alone or together, or in combination with one or more microfilament inhibitors (Shea, 1990). A combination of both microfilament and microtubule inhibitors, at experimentally determined concentrations, can be used to effect complete destabilization of the cytoskeleton.

The age of the donor providing fibroblasts may be another factor in determining "priming" response. Fibroblasts from younger patients may display higher "priming" potential than fibroblasts from older patients and will be examined in initial experiments. Nuclear transfer (NT) experiments in animals indicate that cells derived from younger donors reprogram better and result in higher proportions of NT embryos that complete prenatal development than do embryos created from adult somatic cells (Yang et al., 2000).

The extent of priming itself may prove to be limiting. This could be due to cells' inability to erase nuclear memory to the extent that is required for a change in function. Similarly, donor cells obtained from one cell lineage (i.e. ectoderm) may only be primed to develop into another ectoderm derived cell type. To overcome this potential pitfall, cells will be conditionally immortalized/transformed. Transformed, immortalized cells that can commonly be found in various types of cancer have been shown to be multipotential and can be viewed as "primed" cells. Conditional imortalization of cultured primary cells may be accomplished by transfection with a transgene expressing a mutant, heat labile, form of the SV40 Large T antigen (Bond et al., 1996; SV40tsA58). Cells transgenic for this antigen can be immortalized by culture at 33° C., where the Large T antigen is intact and biologically active. The cells can than be returned to a primary functional state by increasing the incubation temperature to 37° C., where the antigen is truncated and not active at this higher temperature. Since immortalized cells display qualities of de-differentiated cells, they may be more easily primed, then induced to differentiate by supplying the appropriate culture conditions for the desired cell type. At the same time differentiation is induced, the cells can be returned to the non-immortalized state by raising the temperature. This strategy will be employed if difficulty arises in the transdifferentiation of primary cultures (above). Ultimately, if this approach proves to be viable, then the transgene will be flanked with loxp sites, so that it can be removed from the final product using Cre recombinase. We will attempt to induce donor cells to acquire cancer-like characteristics first, and expose them to priming and/or induced differentiation (Cohen et al., 1999).

A second approach to enhancing priming involves manipulation of nuclear structure with drugs that interfere with acetylation and/or methylation. There is a wealth of published literature describing the beneficial effects of deacetylase inhibitors (trichostatin A; Yoshida et al., 1995) and methylase inhibitors (5-aza-cytidine; Boukamp, 1995) on permissiveness of nuclear chromatin for transcription factors, transcription enhancers and other proteins involved in genomic transcription (Kikyo and Wolffe, 2000). Combined use of agents that interfere with acetylation and/or methylation and agents that disrupt the cytoskeleton may allow for shorter priming incubations, more complete reversal of nuclear function and therefore increase the range of cells that can be derived from primed cell populations. Donor cells of choice should have a stable karyotype, have to be able to support expansion in vitro, and survive cryopreservation and subsequent thawing. Some cell types may be better suited for this purpose than others. Also, the long-term effect of ploidy changes induced in trans-differentiated cell will have to be addressed.

2. Utilizing Methods that Effect Induction of Stem Cell Differentiation to Effect Trans-differentiation of Primed Cells.

Conditions for driving embryonic stem and adult stem cells into several terminally differentiated phenotypes have been described (Bain et al., 1995; Pittenger et al., 1999; Fuchs and Segre, 2000; Lee et al., 2000; Bjornson et al., 2000; Schuldiner et al., 2000; Brüstle et al., 1999). Even though we believe "priming" will not turn somatic cells into any type of stem cell, culture conditions that support differentiation of stem cells can be used to support differentiation of "primed" cells. One of the simplest, and best-documented differentiation protocols involves the use of retinoic acid to induce differentiation to neuronal cell precursors. Obtaining differentiated cells of the CNS (e.g. dopaminergic neurons, astrocytes, oligodendrocytes) is a good first step in testing the potency of primed cells, not only because it is the most direct method of obtaining differentiated cells, but also due to the size of the commercial markets for neuronal cell types in the treatment of Parkinson's Disease, Huntington's Disease, Alzheimer's Disease, multiple sclerosis, and repair of spinal cord injury.

Protocols developed for induction of neuronal precursors in mouse ES cells and human neuronal stem cells can be used for inducing the trans-differentiation of primed fibroblasts: serum-free medium, supplemented with retinoic acid, 5 mM ascorbic acid, bFGF2, PDGF on fibrinogen coated culture dishes. All cultures can be maintained in low oxygen environment (2-5%) and 5% $CO_2$ at 36.8° C., as it has been shown that reducing $O_2$ concentration during cell culture dramatically increases the proportion of neuronal precursors that differentiate into dopaminergic neurons (15 to 56%; L. Studer, personal communication). Simultaneously, primed cells can be grown in culture conditions that have been described to support hematopoietic and muscle differentiation pathways (reviewed in Fuchs and Segre, 2000). Cells can be examined for their morphology by time-lapse video imaging and induction of expected gene and protein expression by RT-PCR and ICC, respectively.

TABLE 2

Initial inducing culture conditions for primed cells and expected gene markers

| Expected outcome | culture conditions | induction markers |
|---|---|---|
| Neuronal | bFGF, FGF8, SHH, EGF, PDGF, T3, CNTF | TH, Nurr-1, Pax 3, 5, 8, En-1, FGFR3, GDNF, TUJ1, CalR 4B3, SMP |
| Hematopoietic | RPMI-40, interleukins, GM-CSF, M-CSF, G-CSF, erythropoietin, thrombopoietin | CD14, CD34, CD45 |
| Muscle | BMP-2 | myoD1, skeletal myosin LC, cardiac actin, desmin smooth muscle actin |

Dopamine release can be induced as described (Cibelli et al., 2001). Briefly, culture medium is removed and replaced with Ca-free, Mg-free HBSS. After 15 minutes, this medium is replaced with Ca-free, Mg-free HBSS, supplemented with 56 mM KCl and samples of medium collected after 15-20 minute incubation and stored at −80° C. until assayed.

Data Collection and Analysis: Control, non-primed cells can be grown under the same culture conditions and assayed for both, down-regulation of endogenous genes and proteins, as well as expression of genes induced by culture conditions. The assay for dopamine can be performed by HPLC as described elsewhere. Samples collected prior to KCl induced release can be used for control measurements. In addition to dopamine, the samples can be assayed routinely for serotonin, acetylcholin, and GABA.

Cell type-designed culture conditions will yield cells resembling the expected cell type. Neuronal cell types show induction of gene and protein markers described above. For example, Neurons secrete neuro-transmitters in a time dependent manner that correlates with cell morphology. If required, electrophysiology experiments can be designed to test excitability. Control cells are expected to retain their original phenotype, maintain the corresponding gene and protein expression and show absence of non-specific gene and protein expression. Sufficient cell numbers are available for these analyses since virtually all the primary cells respond to priming, and therefore their numbers can be manipulated by expansion prior to priming.

The gene expression profile specific only to the donor cells is turned off during priming without reversal into a stem cell-like state. In addition, during trans-differentiation, only expression of specific genes corresponding to the predicted types of trans-differentiated cells is turned on.

3. Combinations of Agents Acting on Intracellular Components and Extracellular matrix for Reproducible Induction of a Single Cell Type.

Characterization of the type of cell being formed is an aspect of the present invention. The invention permits analysis and definition of all of the conditions that enable production of functional neurons from fibroblasts. It is useful to determine whether neurons are being produced in a subset of the total population of induced cells. It is known from induction of embryonic stem cells that primarily certain cell types are produced using specific growth factors (GFs) or cytokines. However, these populations are not pure and other cell types persist. Animal serum contains a plethora of proteins and peptides of undefined quantities. Thus, serum contains growth factors and cytokines that support growth and differentiation of essentially all cell types in the body. Therefore, serum-free culture conditions can be developed in order to properly evaluate the effect of specific combinations of GFs and cytokines on differentiation of primed cells. In addition, the effect of various artificial extracellular matrices (ECM) can be tested. The serum-free culture conditions do not necessarily need to induce proliferation but must sustain viability of the cells in vitro. The specific type of culture surface can also be evaluated. Whenever available, human versions of the required growth factors can be used, since the activity of many cytokines is not always equivalent across species.

Due to the human genome project, most of the GFs commercially available are from recombinant human genes. First, primary cell cultures are gradually adapted to serum-free conditions. Then, priming is induced by conditions discussed above. Primed cells in serum-free conditions can be subjected to culture conditions that yield or support specific neural cell types. Growth factors/cytokines that can be used include bFGF, FGF8, SHH, EFG, PDGF, T3, and CNTF. The cell culture surface and ECM materials that can be used include tissue culture plastic, bacterial culture plastic, glass, methylcellulose, fibrinogen, fibronectin, gelatin, collagen, laminin, poly-L-lysine, and poly-L-ornithine. The effect of a selected single GF in combination with a single ECM substrate can be evaluated to optimize conditions. Cells can be assayed for the presence of critical markers for specific cell types using ICC: astrocytes (GFAP), oligodendrocytes (O4), and neurons (TH). The cells produced from induction into neurons can be further assayed for dopamine, serotonin, acetylcholine, and GABA release. Once the interaction between individual growth factor/cytokine and ECM that leads to enrichment of specific neuronal cells types is determined, combinations of GF's/cytokines with the optimal ECM can be evaluated. The GF/cytokine and ECM combination result that leads to the purest population of dopaminergic neurons can thus be determined experimentally.

Gene expression at the RNA level can be determined by RT-PCR and translation products assayed by immunocytochemistry and/or Western blotting. Markers for the expression of specific genes in the differentiated state can be identified depending on the cell type. Immunocytochemistry can also be used to determine the purity of the cell population. RT-PCR primers and hybridization probes and antibodies for ICC and Western blotting are commercially available. Quantitative analysis of gene expression can be analyzed by Northern blots. Temporal changes in morphology can be recorded at regular intervals using time-lapse video imaging. Expression of key marker genes can be monitored at experimentally determined time points to evaluate the timing of priming and differentiation events. This approach yields information as to how long it takes for the donor somatic cell to become responsive to new signals and how long differentiation takes for various cell types.

By the methods described above, a combination of GFs/cytokines and ECM that yields predominantly specific neural cell types can be identified. For example, optimal conditions that yield dopaminergic neurons can be identified. In addition to generation of desired cell types by designed differentiation protocols, undesired cell types may result. Specific growth factor and cytokine combinations may result in an array of cell types, which it may be necessary to characterize. Three-dimensional factorial design of experiments (cytokine×growth factor×matrix) may be performed in conjunction with development of a comprehensive database for tracking cell response. Construction of a reasonably informative database includes catalogued information on donor cell type, primer, priming conditions, timing of gene/protein down regulation, a list of these genes/proteins, induction components, timing and expression of trans-differentiated cell type-specific genes/proteins, a list of these genes and proteins, cell survival and secretory properties (if any).

If cells trans-differentiate into more than one cell type, single cell cloning may be used to generate pure cell populations. It is well established that single cell culture is challenging and many cells do not survive in vitro on their own. Efforts should therefore be made to develop single cell cultures that keep cells physically separated while maintaining the same culture environment. Trans-differentiated cells may have an altered life span. Whether the lifespan is shortened or lengthened can be determined by a longevity analysis, which is routinely performed. If trans-differentiated cells display a shorter lifespan than control donor cells, lifespan can be maintained by reducing $O_2$ concentration during culture to <2%, designing shorter priming protocols, or avoiding excessive in vitro proliferation of donor cells prior to priming.

In addition to the foregoing, injection of primed cells into a live model (mouse) into sites that promote certain cell types can also be performed as a means for effecting trans-differentiation of primed cells.

Finally, trans-differentiation of primed cells can be effected by culturing the primed cells in the presence of other cells that are capable of inducing their neighbors to express specific markers due to paracrine effects. For example, it has been shown that cells transgenic for Pax-8 cause neighboring cells to become dopaminergic neurons (L. Studer, personal communication).

4. Maintain Stable Morphology and Function of Newly Differentiated Cells.

In order for newly differentiated cells to be useful for cell therapy, they must not only attain desired cell shape and function in vitro but also be able to maintain the newly established phenotype/function after trans-differentiation. The maintenance of a stable cell phenotype can be achieved by terminally arresting the cell cycle in $G_0$, an event that is induced in vivo by differentiation itself. While trans-differentiated cells may retain certain nuclear plasticity, appropriate conditions in vitro or in vivo should allow for stabilization of their phenotype. Maintaining the same environmental signals (same medium, same supplemental factors, temperature, and matrix conditions) stabilizes cell phenotype.

Newly trans-differentiated cells can be cultured continuously and monitored at specific time points for expression of cell type-specific markers. Culture occurs in the absence of "priming" agent and under conditions consistent with the "new" cell type. In addition, the cells can be grown in media (or conditions) that are not consistent with the new cell type to evaluate stability. Of particular importance will be the behavior of newly trans-differentiated cells in culture conditions specific for the original donor cell type.

Data Collection and Analysis: Morphology of induced cell can be monitored and progression recorded by video imaging. Gene expression and protein expression/localization can be evaluated by RT-PCR and ICC, respectively for neuronal antigens (neurofilament, enolase, tyrosin hydroxylase, GFAP, dopamine receptor, myelin), muscle specific antigens (β-actin, desmin, myosin heavy chain), and hematopoietic cell markers (CD34).

After withdrawal of the priming agent (e.g., microfilament inhibitor), the cells retain their newly acquired phenotype and either re-enter the cell cycle or remain arrested in $G_0$, depending on the cell phenotype. New neurons are expected to remain in $G_0$ and not proliferate, retain neuronal morphology, secrete neurotransmitters, establish synapses and remain viable for up to 4 days in vitro (Lorenz Studer, personal communication).

It may be challenging to keep population of cells pure since this is not how they grow in vivo. To maintain a stable function in vivo, cells have to interact with their neighboring cells that are of often of a different phenotype (e.g. neurons with glia, muscle with connective tissue and vascular endothelium, etc). It may be necessary to grow new cell types under one of the following two conditions. (1) Growth on a three-dimensional matrix (3-D). This will allow them to establish a more physiological 3-D structure, initiate spatial interactions and start producing their own extracellular matrix. This strategy will be exploited during induction of differentiation. (2) Grow newly differentiated cells on monolayers of cell types with which they would interact normally in vivo.

5. Evaluating Trans-differentiated Cells for Therapeutic Efficacy by in Vivo Cell Transplantation into an Animal Model.

In vivo function of neural cells generated via trans-differentiation from somatic cells is crucial for evaluating therapeutic potential. Several standardized test have been developed in rodents that can reliably mimic clinical symptoms of specific neurological disorders such as Parkinson's disease, Huntington's disease, spinal cord injury, epilepsy or stroke. Transplantation of neurons derived from the developing CNS can significantly improve clinical symptoms in many of these animal models. Cell therapy is especially promising in Parkinson's disease where a relatively small and well-defined population of specific neurons is lost. Clinical transplantation of fetal dopamine neurons has been performed in over 300 patients worldwide and long-term benefit has been demonstrated in patients for at least up to 10 years after transplantation (Piccini et al. 1999). More recently, encouraging results have also been reported for fetal tissue grafting in Huntington's disease (Bachoud-Levi et al. 2000). However, the use of fetal tissue raises significant ethical and technical concerns that have prevented more widespread use of the technology (Freeman et al. 2000). The availability of an easily accessible and renewable source of neural cells will dramatically improve the technical and social outlook of CNS cell transplantation in neurodegenerative disorders. The availability of such a cell source might also obviate the use of immunosuppression in subjects undergoing CNS transplantation and alleviate some of the ethical and psychological concerns of implanting brain cells derived from another individual or species as in the case of fetal pig dopamine neurons (Deacon et al. 1997).

Experimental: Parkinsonian rats and mice are created by unilateral stereotactic injection of the neurotoxin 6-OHDA that is taken up specifically by dopaminergic terminals and retrogradely transported to the cell body where it induces apoptotic cell death. The behavioral outcome of the transplanted cells is assessed using state of the art behavioral tests including rotometer assays. Upon stimulation with drugs that mimic dopamine effects Parkinsonian animals show an asymmetric behavior with postural asymmetry, ipsilateral rotation and contra lateral hemineglect. Animals undergo repeated behavioral tests 2-4 weeks after 6-OHDA injection. Animals with stable behavioral deficits are randomly selected for cell implantation or control group (12 animals each, controls: injection of non-dopaminergic cell or saline). Cells are tested for dopamine production prior to transplantation using non-invasive measurements of dopamine release (Studer et al. 1996; Studer et al. 1998). Upon intrastriatal implantation of functional dopamine neurons Parkinsonian symptoms such as rotation behavior should gradually disappearwithin a period of 4-16 weeks. After completing the behavioral studies the animals are perfused with paraformaldehyde and the brains subjected to immunohistochemical analyses (Studer et al. 1998). Surviving dopamine neurons in the host striatum are identified by immunohistochemistry for tyrosine-hydroxylase, the rate-limiting enzyme in the synthesis of dopamine. Quantification of cell numbers are performed using stereology-based computer assisted counting procedures.

Data Collection and Analysis: Surgical data: We have described our procedures for inducing neurodegenerative lesions as well as performing cell transplantation been described previously in great detail (Tabar and Studer 1997). A hierarchical computer database linked to behavioral and histological results is set up to record all relevant data for each animal included in the study. Behavioral data: Rotation data is collected on a commercially available rotometer system (San Diego Instruments). ASCII files are imported into statistical software for further analyses (Microsoft Excel and Statistica, Statsoft). In vitro functional testing prior to transplantation: Dopamine and serotonin production of the cells to be grafted are assayed using reverse-phase HPLC with electrochemical detection as described previously (Studer et al. 1998; Studer et al. 1996). Data is collected on ESA proprietary software and exported to Statistica (Statsoft) for further analyses. Histological analyses: The number of surviving dopamine neurons in the grafted brain are assessed using stereological counts of Tyrosine-hydroxylase (TH+) cells in the striatum (Studer et al. 1998; Gundersen et al. 1988).

Expected Results: Establishing Parkinsonian lesions in rodents: Typically about 60-80% of the animals subjected to stereotactic 6-OHDA injections show a stable rotation response upon amphetamine injection three weeks after surgery. Recovery of lost function depends on the number and function of the grafted cells. It has been established in fetal tissue grafts that about 1000 rodent dopamine neurons are required to completely restore the rotation behavior of 6-OHDA rodents. The survival rate of dopamine neurons is typically about 5-10%.

Potential Difficulties, Limitations and Alternatives: Animal model: The mouse or rat strain has to be chosen carefully as certain strains show hypersensitivity to some anesthetics such as barbiturates or in some cases various sensitivities to the neurotoxic drugs used. An alternative strain and adaptation in the dose of the neurotoxic drugs would be required. Behavioral test: The degree of Parkinsonian symptoms can vary among animals. Especially in mice the success rate of inducing a stable Parkinsonian lesion is lower and spontaneous recovery has been reported. An alternative strain or neurotoxin can be utilized in such cases. Histology: No difficulties are to be expected if state-of-the-art technical procedures are followed. Alternative disease model: The generation of specific dopamine neurons is challenging. Only about $1:10^4$-$1:10^5$ of all neurons in the adult brain are midbrain dopamine neurons (Hynes and Rosenthal 2000). If no dopamine but other neuronal subtypes are available for grafting, an alternative disease model will be chosen such as ibotenic acid lesion in rodents to mimic Huntington's disease (Tabar and Studer 1997) with subsequent transplantation of neurons exhibiting the more common neurotransmitter GABA.

EXAMPLES

Example 1

Bovine fetal fibroblasts (BFFs) were grown to confluence and seeded onto 100 mm plates at approximately 250,000 cells/plate. Cells were grown in DMEM (Gibco) supplemented with 0.03% L-Glutamine (Sigma), 100 µM non-essential amino acids (Gibco), 10 units/L Penicillin-Streptomycin (Gibco), 154 μM 2-Mercaptoethanol (Gibco) and 15% FBS (HyClone). Four treatments were used:
1. A control grown in the medium described above,
2. DMEM with 2.5 μg/ml CB,
3. DMEM with 5.0 μg/ml CB, and
4. DMEM with 7.5 μg/ml CB.

Control cells were grown in the presence of DMSO alone to evaluate its effect on priming and trans-differentiation.

BFFs cultured in treatment 1 began to rapidly divide and grow to confluence as was expected. BFFs cultured in treatment 2 did not undergo cytokinesis, however did undergo nuclear division leading to multinuclear fibroblasts. BFFs cultured in treatments 3 and 4 began to change morphology and by day 2 of treatment began to take on the appearance of neuronal cells. On day 3 of treatment, a small population of cells that had been grown on glass cover slips were fixed from each of the described treatments, and incubated with an antibody to tyrosine hydroxylase (the rate limiting enzyme involved in dopamine production, specific to neuronal cells). Cells were visualized under fluorescence for detection of antibody labeling. Control cells did not exhibit fluorescence, and cells from groups 2, 3, and 4 fluoresced in a dose-dependent manner, which correlated directly with increasing amounts of CB.

Figure 1:
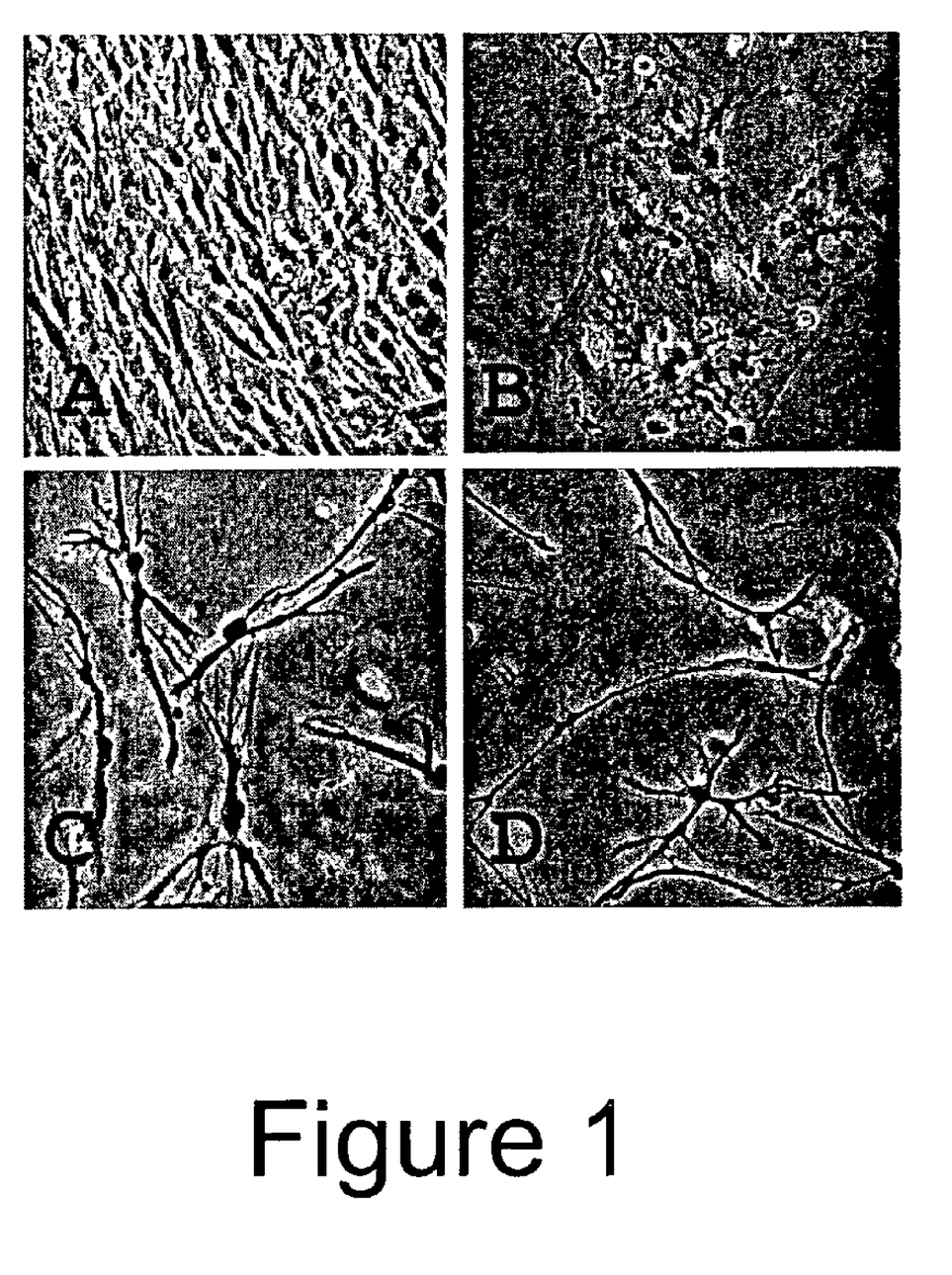
FIGS. 1 and 2: Cells with neuronal morphology produced by treating bovine fetal fibroblasts CB at 2.5-7.5 µg/m and culturing them under conditions that induce neural differentiation. The cells in FIG. 1 were observed with phase contrast microscopy; those in FIG. 2 were observed by DIC.
Figure 2:
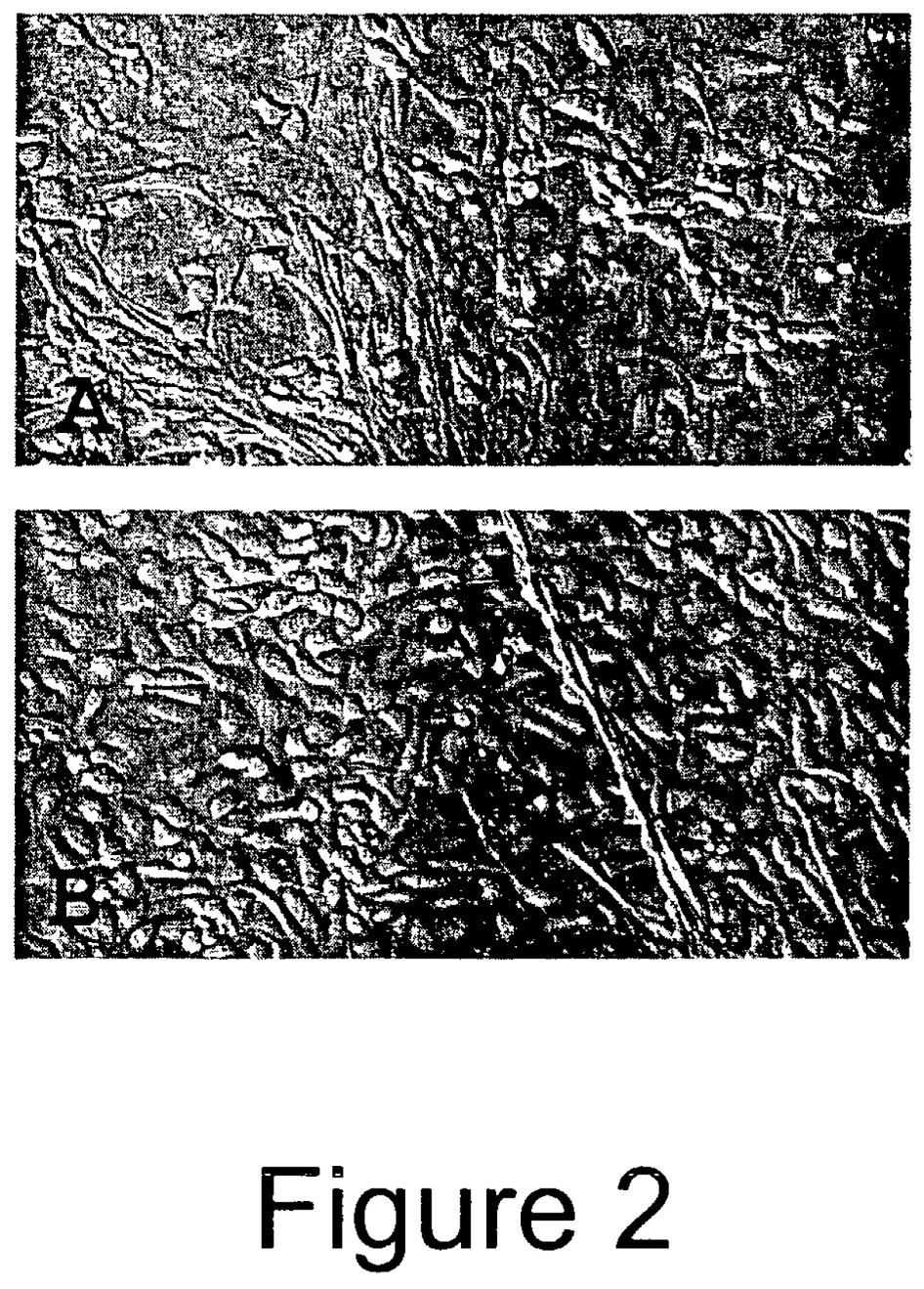
Figure 3:
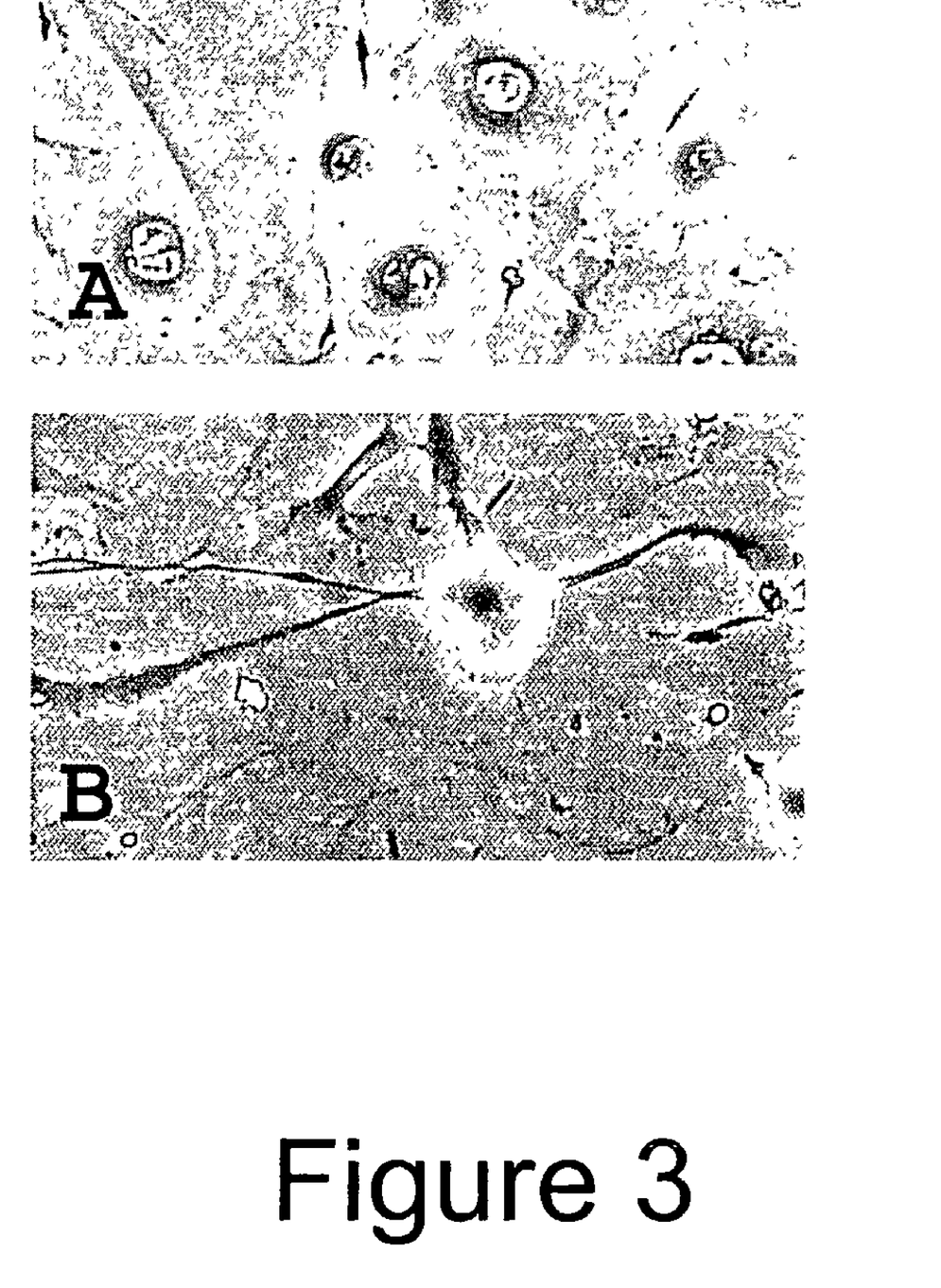
Figure 4:
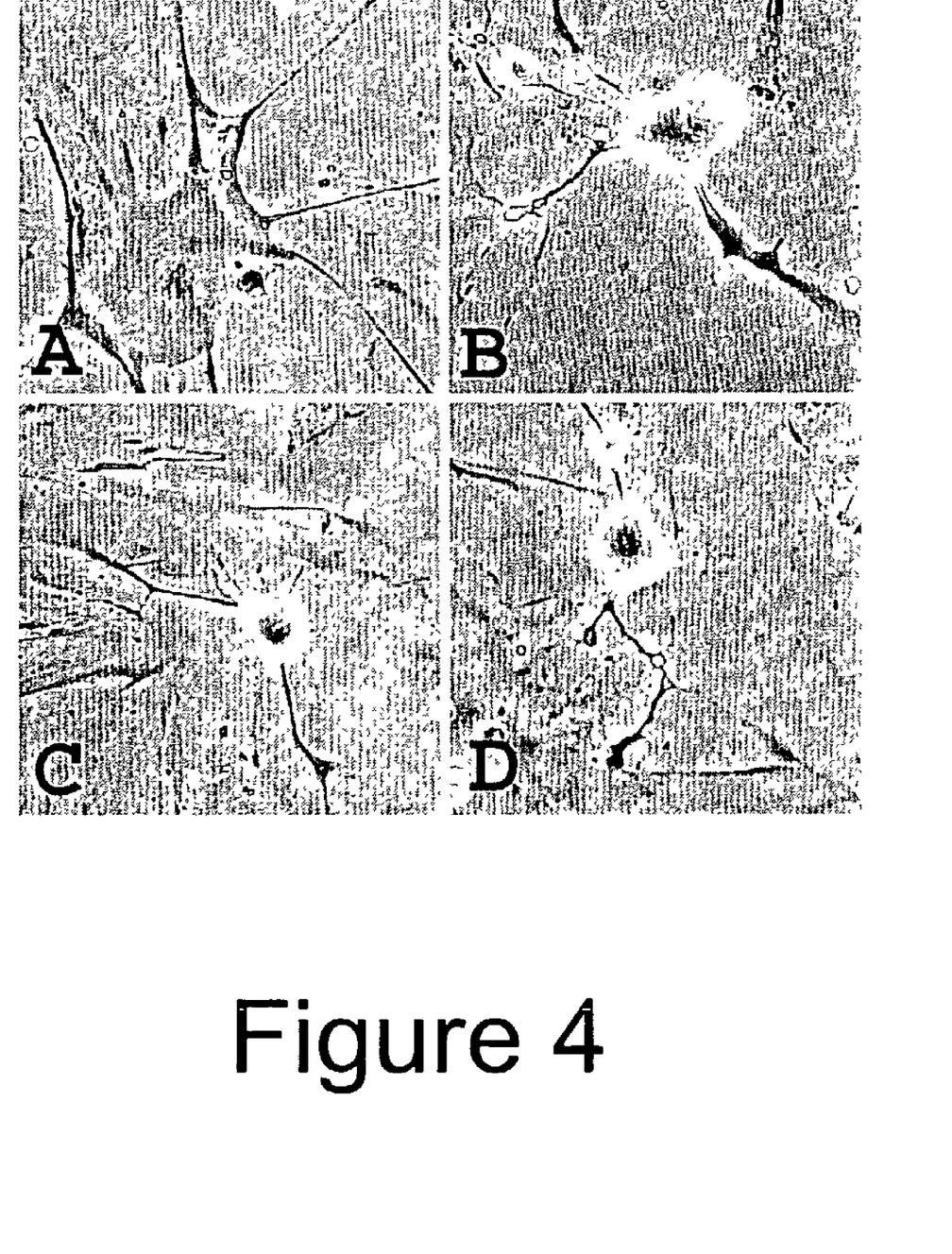

In conclusion, treatment of BFFs with CB at 2.5-7.5 μg/ml is effective at inducing bovine fetal fibroblasts to undergo morphological changes toward a neuronal-like lineage as well as inducing the expression of tyrosine hydroxylase. These results suggest that trans-differentiation can be primed by microfilament inhibitors. Our preliminary data suggest that virtually all the primary fibroblasts (millions from a single patient sample) can be primed within 12-24 hours of in vitro culture. Results are presented in FIGS. 1 and 2.

Example 2

Bovine adult fibroblasts (BAFs) were treated in the manner described for BFFs in Example 1, with priming carried out using 10.0 μg/ml CB for 72 hours. Like BFFs, treatment of the BAFs with the priming agent and culturing them under conditions that induce neural differentiation caused the cells to undergo morphological changes toward a neuronal-like lineage. See FIGS. 3 and 4. Note that BFFs and BAFs acquire different morphologies of a neural type.

Example 3

Figure 5:
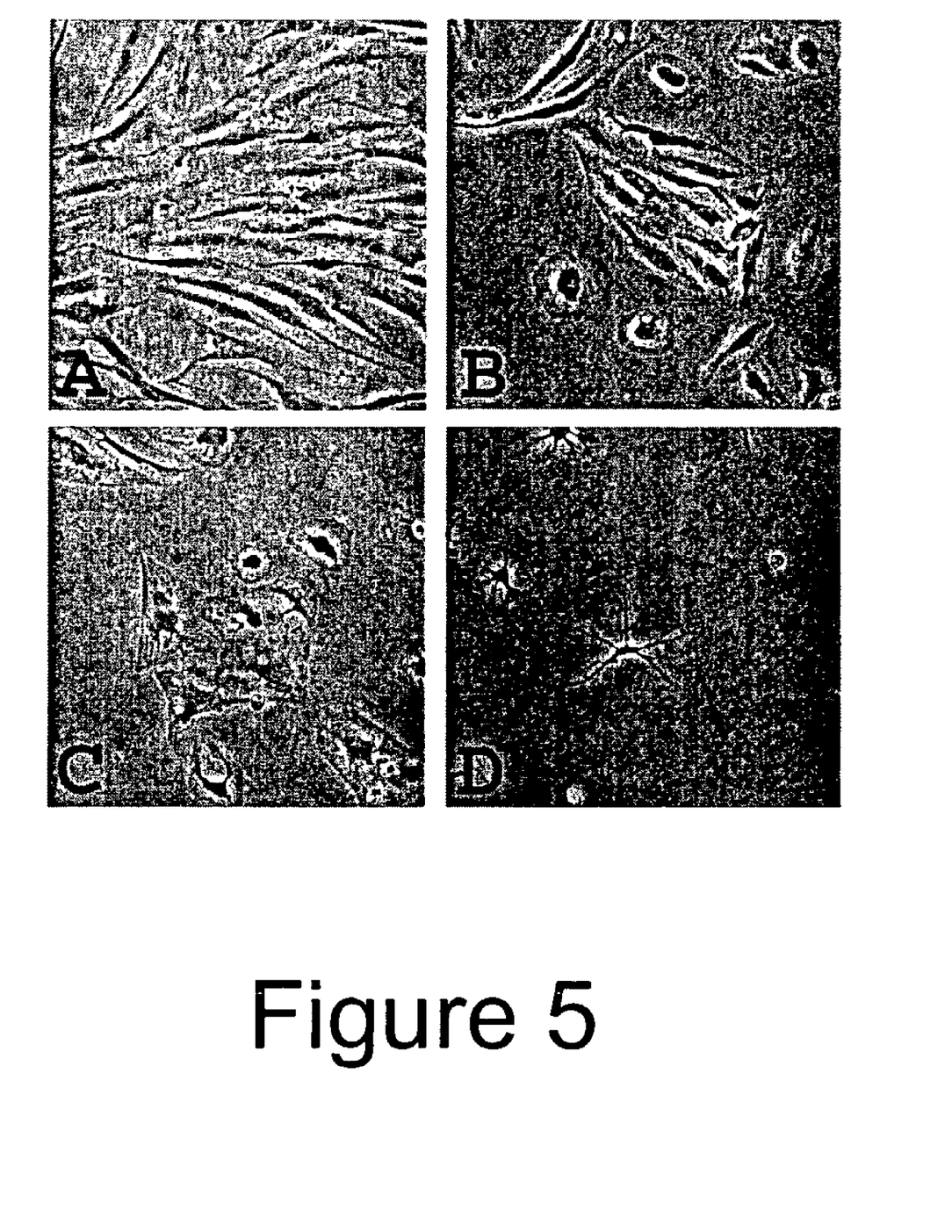
FIG. 5: Cells with neuronal morphology produced by treating human fetal fibroblasts CB at 5.0 µg/m and culturing them under conditions that induce neural differentiation.

Transdifferentiation of human neo-natal fibroblasts. Fibroblasts were purchased from Cambrex company (Clonetics cell line #CC-2509) and were expanded in Iscove's Modified Dulbecco's Medium (IMDM, Gibco) supplemented with 20% fetal bovine serum (HyClone) at 37° C. in 5% $CO_2$ and 5% $O_2$. At passage 14, cells were weaned from serum by replacing medium every other day with half the concentration of serum over a 2-week period. When cells had been in the absence of serum for 48 hours, they were seeded at 50% confluency in 24-well dishes. 24 hours after passage, IMDM was removed and replaced with conducive medium (keratinocyte growth medium (KGM, Clonetics) was added to half of the cultures and neuro-progenitor growth medium (NPMM, Clonetics) was added to the other half). After 24 hours in conducive medium, 5 μg/ml cytochalasin B (CB, CalBiochem) was supplemented into half of each media group. Cells were cultured for an additional 72 hours at which point half of all groups were fixed in 4% paraformaldehyde (Sigma) in Dulbecco's phosphate-buffered saline (DPBS, Biowhittaker), and the remaining half were replaced with fresh medium (KGM and NPMM respectively) without CB. These cells were then cultured for another 72 hours at which point they were fixed in 4% paraformaldehyde in DPBS. As with BFFs and BAFs, treatment of the human fetal fibroblasts BFFs with CB at 5 μg/ml and culturing them under conditions that induce neural differentiation is effective at inducing the fibroblasts to undergo morphological changes toward a neuronal-like lineage (see FIG. 5).

Figure 6:
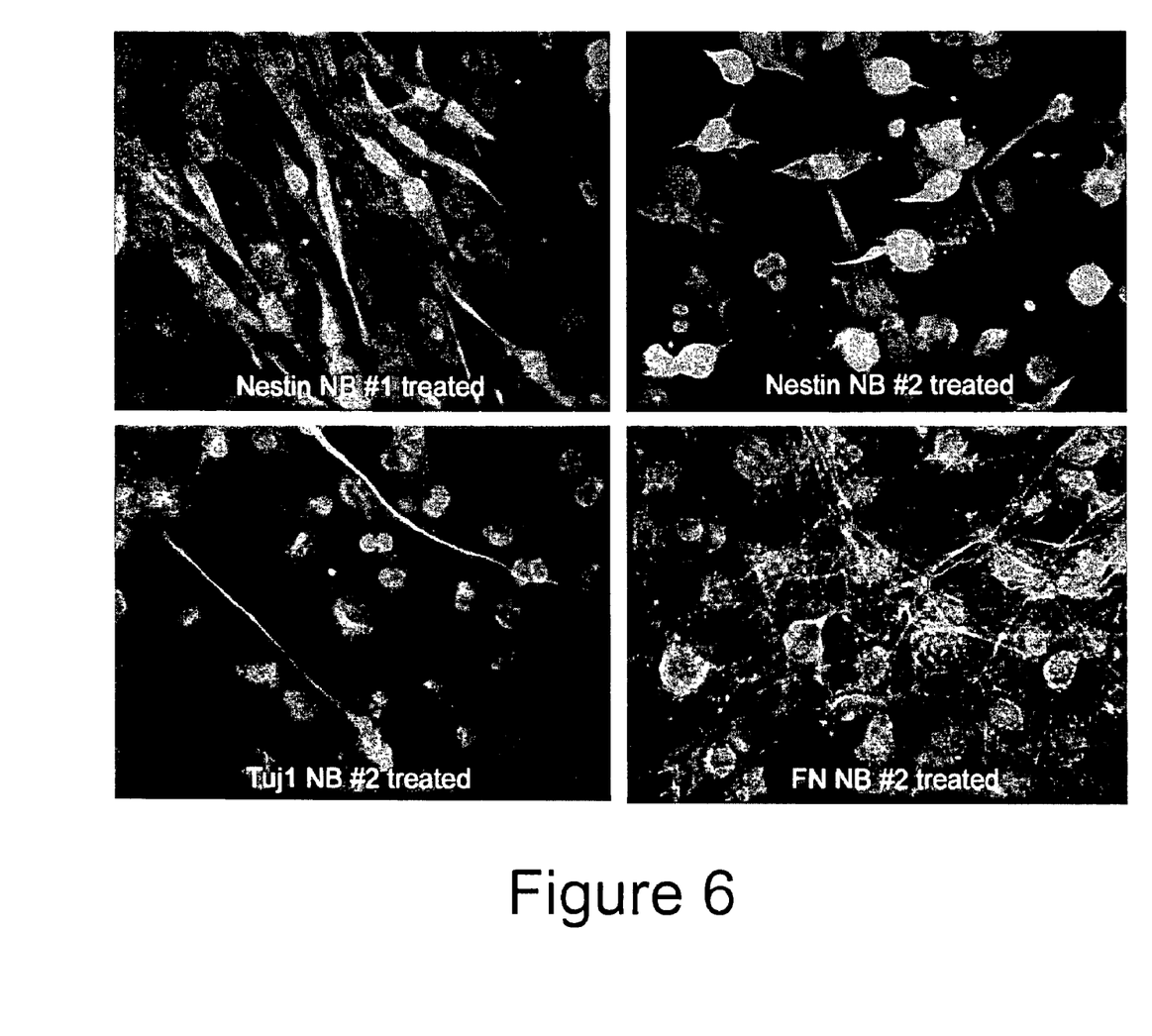
FIG. 6: Photographs showing the presence of neural-specific markers nestin and Tuj1 in human fetal fibroblasts treated with CB at 5.0 µg/m and cultured under conditions that induce neural differentiation.

Immunocytochemistry was conducted using antibodies to Nestin, Glial Fibriliary Acid Protein (GFAP), Oligo 4 (O4), beta Tubulin III, Tuj1, Gamma Amino Buteric Acid (GABA), Tyrosine Hydoxylase, MAP2ab, Calretinin, Tropomyosin. Cells treated with cytochalasin B were positive for markers of cells of neuronal lineage-nestin, Tuj-1, and beta tubulin III (see FIG. 6). The control fibroblasts not treated with CB were negative for all markers. Nestin is an intermediate microfilament present in neural stem cells prior to terminal differentiation. Tuj-1 is a neuron-specific tubulin, and beta Tubulin III is a microtubule that is present only in neurons.

REFERENCES

Bachoud-Levi A C et al., Lancet (2000) 356
Bain G et al., Dev Biol (1995) 168:342-357
Basic Cell Culture Protocols (Pollard and Walker, eds.), Humana Press, 1997
Bjornson C R R et al., Science (1999) 283:534-537
Black I et al., J Neurosci (2000)
Bond J A et al., Int J Cancer (1996) 67:563-572
Boukamp P, Semin Cell Biol (1995) 6:157-163
Bouwens L, J Pathol (1998b) 184:234-239
Bouwens L, Microsc Res Tech (1 998a) 43:332-336
Brown P D and Benya P D, J Cell Biol (1988) 106:171-179
Brüstle O et al., Science (1999) 285:754-756
Cibelli J et a., Science (2001) in press
Clark M S et al., J Neurosci (1995) 15:6167-6178
Cohen E et al., J Cell Sci (1999) 112:2657-2666
Deacon T et al., Nature Med (1997) 3:350-353
Eguchi G and Kodama R, Curr Opin Cell Biol (1993) 5:1023-1028
Fernandez-Valle C et al., J Neurosci (1997) 17:241-250
Fraichard A et al., J Cell Sci (1995) 108:3181-3188
Freeman T B et al., Proc Natl Acad Sci USA (2000) 97:13877-13882
Fuchs E and Segre J A, Cell (2000) 100:143-155
Gundersen H J G et al., APIMS (1988) 96:379-394
Hallows K R and Frank R C, Biorheology (1992) 29:295-309
Hamano T and Asofsky R, J Immunol (1984) 132:122-128
Hay E D and Zuk A, Am J Kidney Dis (1995) 26:678-690
Hoerger T J et al., Pharmacokinetics (1998) 14:541-557
Hohn H P and Denker H W, Exp Cell Res (1994) 215:40-50
Holtzer h et al., Proc Natl Acad Sci USA (1975) 72:513-517
Hynes M and Rosenthal A, Neuron (2000) 28:11-14
Imaizumi T et al., Nature Biotech (2000) 18:949-953
Keller G M, Curr Opin Cell Biol (1995) 7:862-869
Kikyo N and Wolffe A P, J Cell Sci (2000) 113:11-20
Kishkina V B et al., Biull Eksp Biol Med (1983) 96:97-99
Kopyov O V et al., Cell Transplantation (1996) 5:327-337
Lang A E, Archives Neurol (2000) 57:1118-1125
Lee S H et al., Nature Biotech (2000) 18:675-679
Leno G H et al., Cell (1992) 69:151-158
Levit K et al., Health Affairs (1998) 17:99-110
Nathanson M A, Curr Top Dev Biol (1986) 20:39-62
Ng Y Y et al., Nephrol Dial Transplant (1999) 14:28602872
Okado H and Takahashi K, Proc Natl Acad Sci USA (1988) 85:6197-6201
Okado H and Takahashi K, J Physiol (1990) 427:583-602

Okado H and Takahashi K, J Physiol (1990) 427:603-623
Pairault J and Lasnier F, Biol Cell (1987) 61:149-154
Paterson F C and Rudland P S, J Cell Physiol (1985) 125: 135-150
Piccini P et al., Nature Neurosci (1999) 2:1137-1140
Pittenger M F et al., Science (1999) 284:143-147
Pratt H P et al., Cell (1981) 26:279-292
Rosen D M et al., Exp Cell Res (1986) 165:127-138
Sato K et al., Rinsho Shinkeigaku (1991) 31:809-814
Schmidt V and Alder H, Cell (1984) 38:801-809
Schuldiner M et al., Proc Natl Acad Sci USA (2000) 97:11307-11312
Shea T B, Cell Biol Int Rep (1990) 14:967-979
Siderowf A D et al., Movement Disorders (2000) 15:439-455
Strutz F and Muller G A, Nephrol Dial Transplant (2000) 15:1729-1731
Studer L et al., Brain Res Bull (1996) 41:143-150
Studer L et al., Nature Neurosci (1998) 1:290-295
Tabar V and Studer L (1997) Transplantation into the adult rodent brain, in Current Protocols in Neuroscience (McKay R D and Gerfen C R, eds.), John Wiley & Sons Inc., New York
Takigawa M et al., Cell Differ (1984) 14:197-204
Tamai K et al., Dev Growth Differ (1999) 41:41-49
Theise N D et al., Hepatology (2000) 32:11-16
Ulloa L and Avila J, Eur J Neurosci (1996) 8:1441-1451
van der Loo W et al., J Immunol 91979) 122:1203-1208
Whetton-Goldstein K et al., JAGS (1997) 45:844-849
Wright W E, J Cell Biol (1984) 98:427-435
Wu C F et al., J Neurobiol (1990) 21:499-507
Yan J et al., J Neurochem (2001) 76:307-311
Yang X et al., Biol Reprod (2000)
Yeomans N D et al., Gastroenterology (1976) 71:770-777
Yoshida M et al., BioEssays (1995) 17:423-430
Yuan S et al., Differentiation (1996) 61-:67-75
Yujiri T et al., J Biol Chem (1999) 274:12605-12610
Zanetti N C and Solursh M, J Cell Biol (1984) 99:115-123
Zawada W M et al. Nature Med (1998) 4:569-573

What is claimed:

1. A method for converting a bovine fibroblast or a human fibroblast into a cell of neuronal cell type, the method comprising:(a) culturing the bovine fibroblast or the human fibroblast in the presence of 0.1 to 10 μg/ml cytochalasin B, and optionally, at least one inhibitor of acetylation, at least one inhibitor of methylation, or a mixture thereof, wherein the culturing is in the absence of a cell permeablizing agent; (b) culturing the fibroblast in the presence of an agent or a condition that induces differentiation of a multipotent cell capable of differentiating into a neuronal cell type into a neuronal cell type wherein step (b) is performed after step (a); and (c) identifying the cell of neuronal cell type from the culture of step (a) and step (b).

2. The method of claim 1, further comprising culturing the fibroblast in serum-free medium before performing step (a) or prior to performing step (b).

3. The method of claim 1, wherein the at least one inhibitor of acetylation is a deacetylase inhibitor.

4. The method of claim 1, wherein the at least one inhibitor of methylation is a methylase inhibitor.

5. The method of claim 1, further comprising culturing the fibroblast in serum-free medium prior to performing step (b).

6. The method of claim 1, further comprising culturing the fibroblast is cultured in keratinocyte growth medium or neuro-progenitor growth medium before performing step (a) or prior to performing step (b).

7. The method of claim 1, wherein the cell of neuronal cell type is identified by detection of a marker of cells of neuronal cell type.

8. The method of claim 7, wherein the marker of cells of neuronal cell type is selected from the group consisting of TH, Nurr-1, Pax 3, Pax 5, Pax 8, En-1, FGFR3, GDNF, TUJ1, CalR, 4B3, and SMP.

9. The method of claim 1, wherein the agent or the condition that induces differentiation into a cell of neuronal cell type is retinoic acid.

10. The method of claim 1, wherein the agent or the condition that induces differentiation into the cell of neuronal cell type is selected from the group consisting of bFGF, FGF8, SHH, EGF, PDGF, T3, and CNTF.

11. A method for converting a bovine fibroblast or a human fibroblast into a cell of neuronal cell type, the method comprising:(a) culturing the bovine fibroblast or the human fibroblast in the presence of 0.1 to 10 μg/ml cytochalasin B, and optionally, at least one inhibitor of acetylation, at least one inhibitor of methylation, or a mixture thereof; (b) culturing the fibroblast in the presence of an agent or a condition that induces differentiation of a multipotent cell capable of differentiating into a neuronal cell type into a neuronal cell type wherein step (b) is performed after step (a); and (c) identifying the cell of neuronal cell type from the culture of step (a) and step (b) wherein: the culturing of step (a) is in the presence of the deacetylase inhibitor; the culturing of step (a) is in the presence of the methylase inhibitor; the cell of neuronal cell type is identified by detection of a marker of cells of neuronal cell type selected from the group consisting of TH, Nurr-1, Pax 3, Pax 5, Pax 8, En-1, FGFR3, GDNF, TUJ1, CalR, 4B3, and SMP; or the agent or the condition that induces differentiation into the cell of neuronal cell type of step (b) is retinoic acid.

12. The method of claim 11, wherein the culturing of step (a) is in the presence of the deacetylase inhibitor.

13. The method of claim 11, wherein the culturing of step (a) is in the presence of the methylase inhibitor.

14. The method of claim 11, wherein the cell of neuronal cell type is identified by detection of a marker of cells of neuronal cell type selected from the group consisting of TH, Nurr-1, Pax 3, Pax 5, Pax 8, En-1, FGFR3, GDNF, TUJ1, CalR, 4B3, and SMP.

15. The method of claim 11, wherein the agent or the condition that induces differentiation into the cell of neuronal cell type of step (b) is retinoic acid.

* * * * *